United States Patent
Sinha

(10) Patent No.: US 9,354,094 B2
(45) Date of Patent: May 31, 2016

(54) APPARATUS AND METHOD FOR NONINVASIVE PARTICLE DETECTION USING DOPPLER SPECTROSCOPY

(75) Inventor: Dipen N. Sinha, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 256 days.

(21) Appl. No.: 13/225,750

(22) Filed: Sep. 6, 2011

(65) Prior Publication Data

US 2012/0055264 A1 Mar. 8, 2012

Related U.S. Application Data

(60) Provisional application No. 61/379,881, filed on Sep. 3, 2010.

(51) Int. Cl.
G01F 1/74 (2006.01)
G01F 1/66 (2006.01)
G01F 1/704 (2006.01)

(52) U.S. Cl.
CPC ............. *G01F 1/663* (2013.01); *G01F 1/704* (2013.01); *G01F 1/74* (2013.01)

(58) Field of Classification Search
USPC ........ 73/61.41–61.79, 64.53, 861.25–861.31, 73/628; 702/54; 324/76.77, 76.78
See application file for complete search history.

(56) References Cited

U.S. PATENT DOCUMENTS

| | | | |
|---|---|---|---|
| 3,178,940 A * | 4/1965 | Dahlke et al. | 73/861.26 |
| 4,103,679 A * | 8/1978 | Aronson | 600/456 |
| 4,246,653 A | 1/1981 | Malm | |
| 4,279,167 A * | 7/1981 | Erb et al. | 73/861.25 |
| 4,280,365 A | 7/1981 | Connery et al. | |
| 4,542,644 A * | 9/1985 | Claytor et al. | 73/61.75 |
| 4,689,986 A * | 9/1987 | Carson et al. | 73/19.03 |
| 4,909,081 A * | 3/1990 | Kulczyk et al. | 73/597 |
| 5,103,827 A * | 4/1992 | Smith | 600/454 |
| 5,719,329 A * | 2/1998 | Jepson et al. | 73/61.49 |
| 6,065,350 A * | 5/2000 | Hill et al. | 73/861.27 |
| 6,212,951 B1 * | 4/2001 | Derevyagin | 73/335.01 |
| 6,324,901 B1 * | 12/2001 | Fluh et al. | 73/61.75 |
| 6,378,357 B1 * | 4/2002 | Han et al. | 73/54.41 |
| 6,401,538 B1 * | 6/2002 | Han et al. | 73/599 |
| 6,748,811 B1 * | 6/2004 | Iwanaga et al. | 73/861.27 |
| 6,782,751 B2 * | 8/2004 | Linares et al. | 73/622 |
| 6,931,945 B2 * | 8/2005 | Takeda et al. | 73/861.25 |
| 7,260,482 B2 * | 8/2007 | Volker et al. | 702/22 |
| 8,364,421 B2 * | 1/2013 | Chen et al. | 702/25 |

(Continued)

*Primary Examiner* — Peter Macchiarolo
*Assistant Examiner* — Alexander Mercado
(74) *Attorney, Agent, or Firm* — Samuel M. Freund; Cochran Freund & Young, LLC

(57) ABSTRACT

An apparatus and method for noninvasively detecting the presence of solid particulate matter suspended in a fluid flowing through a pipe or an oil and gas wellbore are described. Fluid flowing through a conduit containing the particulate solids is exposed to a fixed frequency (>1 MHz) of ultrasonic vibrations from a transducer attached to the outside of the pipe. The returning Doppler frequency shifted signal derived from the scattering of sound from the moving solid particles is detected by an adjacent transducer. The transmitted signal and the Doppler signal are combined to provide sensitive particulate detection. The magnitude of the signal and the Doppler frequency shift are used to determine the particle size distribution and the velocity of the particles. Measurement of the phase shift between the applied frequency and the detected Doppler shifted may be used to determine the direction of motion of the particles.

15 Claims, 9 Drawing Sheets

(56) References Cited

U.S. PATENT DOCUMENTS

| | | | |
|---|---|---|---|
| 2002/0011120 A1* | 1/2002 | Huang | 73/861.25 |
| 2002/0083771 A1* | 7/2002 | Khuri-Yakub et al. | 73/589 |
| 2004/0065160 A1* | 4/2004 | Povey et al. | 73/865.5 |
| 2004/0144175 A1* | 7/2004 | Sinha | 73/579 |
| 2005/0109112 A1* | 5/2005 | Gysling et al. | 73/587 |
| 2005/0210965 A1 | 9/2005 | Sinha | |
| 2005/0262927 A1* | 12/2005 | Scott | 73/64.53 |
| 2006/0005611 A1* | 1/2006 | Betz | 73/61.75 |
| 2007/0175280 A1* | 8/2007 | Johansen | 73/599 |
| 2007/0293759 A1* | 12/2007 | Eilers et al. | 600/454 |
| 2008/0173100 A1* | 7/2008 | Davis | 73/861.27 |
| 2008/0184784 A1* | 8/2008 | Dam | 73/61.75 |
| 2008/0245137 A1* | 10/2008 | Tavlarides et al. | 73/61.75 |
| 2008/0252283 A1* | 10/2008 | McAnally et al. | 324/76.78 |
| 2009/0025460 A1* | 1/2009 | Hurmuzlu et al. | 73/61.45 |
| 2009/0084178 A1 | 4/2009 | Sinha | |
| 2009/0211347 A1* | 8/2009 | Berger et al. | 73/64.53 |
| 2010/0000325 A1* | 1/2010 | Kaduchak et al. | 73/570.5 |
| 2011/0041590 A1* | 2/2011 | Oddie et al. | 73/64.53 |
| 2012/0226163 A1* | 9/2012 | Moehring et al. | 600/454 |

\* cited by examiner

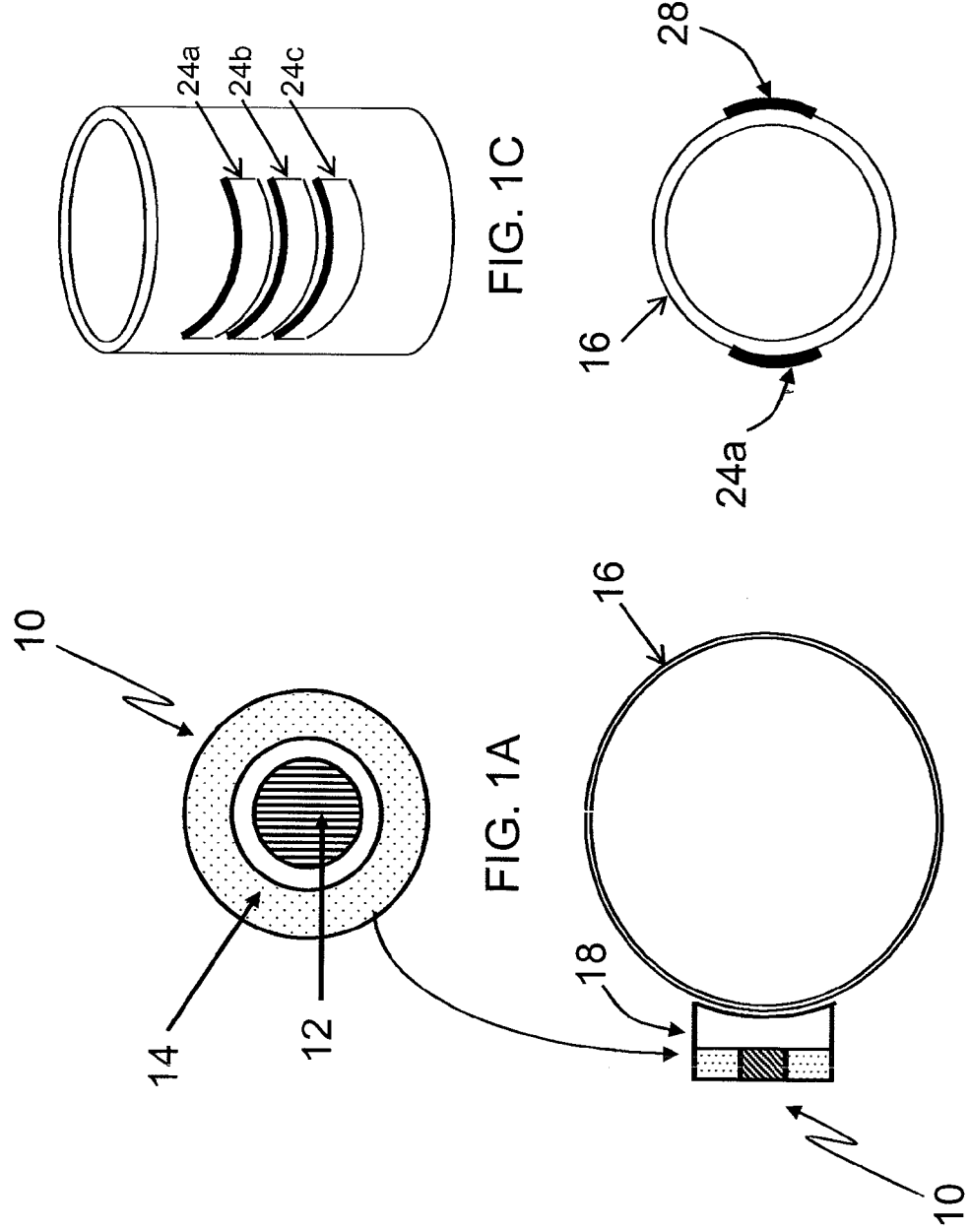

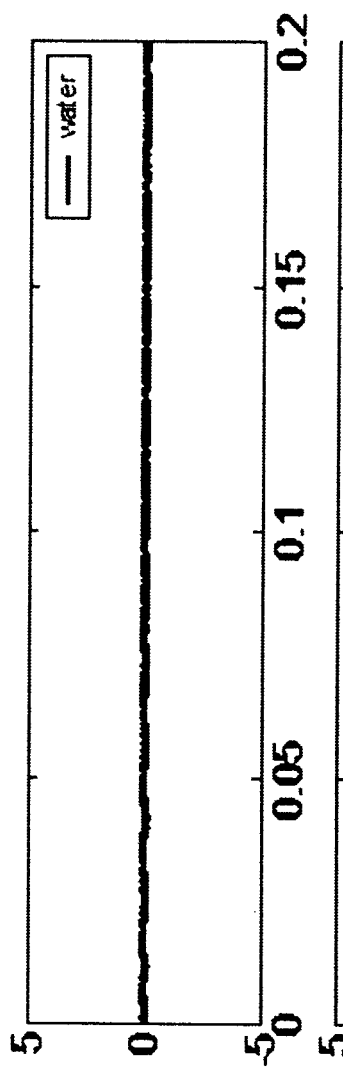
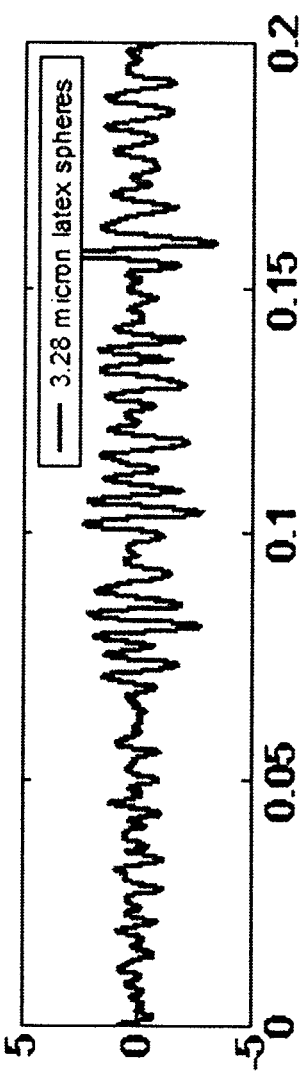
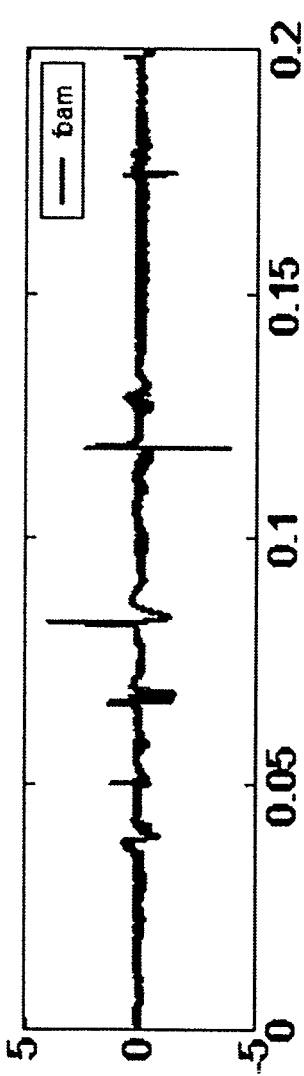
FIG. 9A
FIG. 9B
FIG. 9C

APPARATUS AND METHOD FOR NONINVASIVE PARTICLE DETECTION USING DOPPLER SPECTROSCOPY

CROSS-REFERENCE TO RELATED APPLICATIONS

The present application claims the benefit of U.S. Provisional patent application No. 61/379,881 for "Method And Apparatus For Noninvasive Solid Particle Detection Using Doppler Spectroscopy" which was filed on Sep. 3, 2010, the entire contents of which is hereby specifically incorporated by reference herein for all that it discloses and teaches.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to an apparatus and method for detecting particles in flowing fluids and, more particularly to an accurate, noninvasive, movable apparatus for detecting particles in flowing fluids.

BACKGROUND OF THE INVENTION

Detection of the presence of solid particles such as sand and a determination of the quantity of produced sand in well bore pipes and other flow systems is important for maximizing oil/gas production rates by avoiding severe damage caused by the sand. Sand may clog well lines, thereby adversely affecting production, and can also contaminate separator tanks. Once sand enters a well pipeline, severe corrosion and/or erosion are likely requiring expensive removal of deep sea and down hole pipelines. Sand production may begin with relatively small quantities, which may then rapidly increase.

There are several currently available techniques for detecting the presence of particulates in a fluid flow-stream. One technique continuously senses the vibration produced by sand impacting a pipe or conduit in which a fluid containing sand flows. Such devices, for example the ClampOn™ meter, are affixed to the pipe, typically at an elbow or at a section of the pipe where the flow has to make an abrupt turn, and use passive ultrasonic listening to detect the vibrations when the sand impacts the pipe. Obvious limitations of such passive listening techniques are that they cannot be used for the straight portions of the pipe or only slightly bending pipes. Passive listening techniques are also affected by ambient noise, which can only be partially compensated for. Other techniques include inserting probes into the fluid flow line that convert the sand impact on the probe to electrical signals.

SUMMARY OF THE INVENTION

Embodiments of the present invention overcome the disadvantages and limitations of the prior art by providing an apparatus and method for detection of solids in flowing fluids.

Another object of embodiments of the invention is to provide an apparatus and method for the noninvasive detection of solids in flowing fluids.

It is another object of embodiments of the invention to provide an apparatus and method for detection of solids in flowing fluids that can be attached at any location of a production pipe and readily moved to another location.

A further object of embodiments of the present invention is to provide an apparatus and method for the noninvasive detection of solids in flowing fluids which can detect both small and large quantities of particles.

Yet another object of embodiments of the present invention is to provide an apparatus and method for the accurate, noninvasive detection of small quantities of solids present in flowing fluids.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for noninvasively detecting at least one particle suspended in a fluid flowing in a pipe having an axis and a wall, hereof includes: a first transducer in vibrational communication with an outside surface of the pipe at a chosen position along the axis thereof; a signal generator for providing a chosen signal having at least one selected frequency to the first ultrasonic transducer, wherein vibrations are generated in the fluid at least a portion of which vibrations are in the direction of flow of the fluid; a second transducer in vibrational communication with an outside surface of the pipe disposed alongside the first transducer at the chosen position along the axis, for detecting a scattered vibration signal from the at least one particle; and means for monitoring a Doppler frequency shift between the detected scattered signal from the at least one particle and the chosen vibration signal generated by the first transducer; whereby the at least one particle is detected.

In another aspect of the present invention and in accordance with its objects and purposes the method for noninvasively detecting at least one particle in a fluid flowing in a pipe having an axis and a wall, hereof, includes: generating vibrations having at least one chosen frequency in the fluid in the direction of fluid flow; detecting a scattered vibration signal from the at least one particle; and monitoring the Doppler frequency shift between the scattered vibration signal from the at least one particle and the chosen frequency of the generated vibrations; whereby the at least one particle is detected Benefits and advantages of embodiments of the present invention include, but are not limited to, providing a noninvasive apparatus and method for determining whether particulates are present in a fluid flowing through a pipe, which may utilize high frequencies (~MHz), which generally eliminate ambient noise and which can be tuned to a pipe wall thickness mode resonance for optimization of Doppler signals, which can detect both particle size and total volume of particles since the signal strength depends on the volume of scatterers and the spectrum is related to particle size and distribution, including single particles greater than 1 µm for laminar flow of single phase fluid, which may combine both direct sound transmission measurements and Doppler measurements, and which may be attached at any location along the exterior of a production pipe and readily moved to another location as becomes necessary.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of a top view of an embodiment of the dual-element piezoelectric transducer having a disk piezoelectric transducer surrounded by a ring piezoelectric transducer, where the disk transducer is used as the transmitter and ring transducer is used as the receiver, FIG. 1B is a schematic representation of a top view of the transducer shown in FIG. 1A mounted on the outer surface of a pipe, illustrating a coupler having a flat surface on one side, and curved surface on the other to match the curvature of the pipe, and FIGS. 1C and 1D are schematic representations of a perspective view of the pipe and a top view thereof, respectively, having parallel curved piezoelectric material strips which match the curvature of the pipe attached thereto.

FIG. 9A is a graph illustrating that when only water is present without particles, there is no Doppler signal, and FIG. 9B is a graph illustrating the Doppler signal when 3.28 μm latex particles were introduced into the flowing water, and FIG. 9C is a graph illustrating the Doppler effect for a water/mineral oil foam.

DETAILED DESCRIPTION OF THE INVENTION

Figures 2A, 2B:
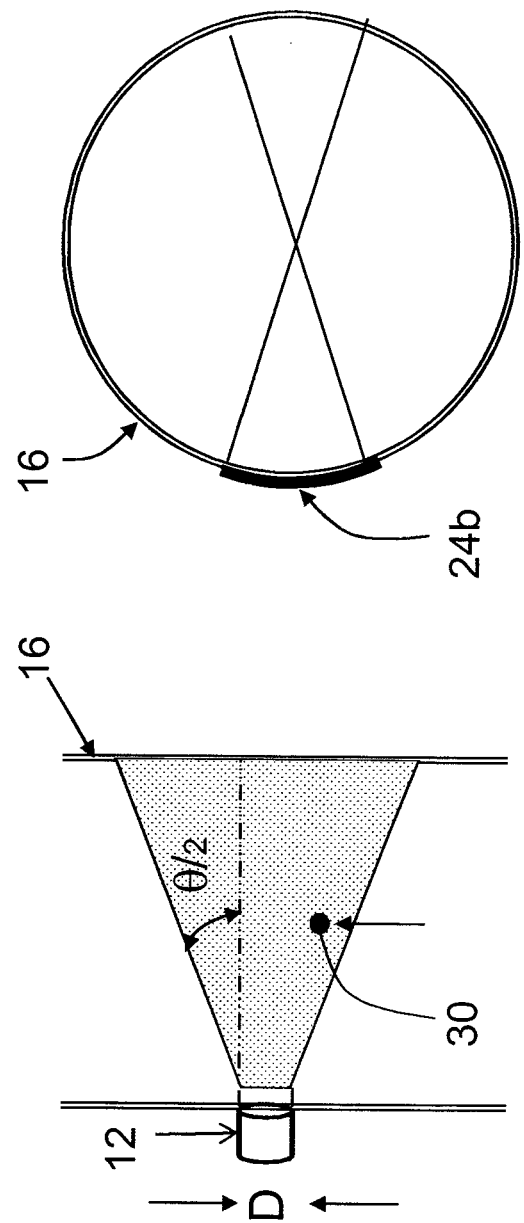
FIG. 2A illustrates the transducer sound beam spread along the pipe axis for the dual-element transducer shown in FIG. 1A, whereas the circumferential beam profile for a curved transducer coupled to the pipe is shown in FIG. 2B, hereof.

Briefly, embodiments of the present invention include an apparatus and method for noninvasively detecting the presence of solid particulate matter, such as sand, suspended in a fluid flowing through a conduit or pipe, such as might be encountered down-hole in an oil or gas well. High frequency (>1 MHz) ultrasonic Doppler spectroscopy is used to detect particles and to measure the particle size distribution. A volume of fluid flowing through a conduit containing the particulate solids is exposed to a fixed frequency of ultrasonic vibrations from a transducer that is attached to the outside of the pipe. The returning frequency shifted signal derived from the scattering of sound from the moving solid particles is detected by an adjacent transducer. The high frequency used is typically above external and ambient noise present in production locations, and sound transmission through the conduit wall is maximized by selecting frequencies that correspond to the thickness mode resonance of the wall, which also serves as a narrow band-pass filter and makes the present system substantially immune to external noise. The present invention combines the transmitted signal and the Doppler signal to provide sensitive sand detection. Both the magnitude of the signal and the Doppler frequency shift are used to determine the characteristics of the particles, such as the distribution of particle sizes, and the spectrum of the Doppler shift signal may be used to determine the velocity of the particles.

Small, dual-element ultrasonic transducers may be used, or in another embodiment, a set of curved transducers which match the curvature of the pipe is used. The particular type of transducer is determined based on the ease of implementation for a particular application. The beam spread of the transducers in the fluid inside the pipe should be sufficient to carry out the Doppler measurement. The transducers do not require any special preparation and can be mounted anywhere on the exterior of the pipe wall.

The present invention differs from the prior art in that impact vibrations produced by the sand particles colliding with each other, with the internal surfaces of the pipe, or with an internal probe, are not measured. Therefore, the present invention does not require that sensors are attached to an "elbow" or a section of the pipe that has an abrupt turn. Sound transmission is also affected when large number of particles passes through the system.

In accordance with embodiments of the present invention, the Doppler measurement utilizes transmitting and receiving transducers on the same side of the flowing liquid. An I-Q (in phase and quadrature) demodulator is a device that mixes the transmitting with the receiver output frequencies to extract the difference frequency. However the demodulator includes two mixers operating at 90° from each other, for example sine and cosine functions. That is, the Doppler signal is a vector signal and I and Q provide the information of the vector in the x and y directions. Such information is not required if only the speed of the particles is of interest, in which situation only the magnitude of the difference frequency signal is needed. However, this information does not provide directional information. The I-Q demodulator also provides phase information, from which the direction of movement can be determined. The apparatus described in more detail hereinbelow accomplishes both functions.

The apparatus also makes use of a receiving transducer on the opposite side of the pipe from the transmitting transducer for determining wall thickness resonances where the sound transmission is the maximum, as will be described in more detail hereinbelow. Once these so-called transmission windows are located, one uses any of those frequencies for the Doppler measurement. Higher frequencies provide higher difference frequency signals for the same speed, and are therefore more sensitive. However, higher frequency also narrows the beam width of the transducer. Thus, a particular transmission window may be selected for any given measurement. This is not always required depending on the wall thickness of the pipe: if the wall is thick then resonance peaks are closely spaced, any one may be chosen without noticeable difficulty. However, for thin wall pipes, the transmission windows are far apart and an appropriate frequency may be selected, although the apparatus will perform reasonably well regardless of whether one chooses an appropriate transmission window. Choice of a suitable transmission window fine tunes the apparatus for efficient operation.

If the temperature of the liquid changes significantly (for example, during steam injection for loosening oil downhole) the temperature of the pipe wall changes and shifts the resonance frequencies slightly. As will be described hereinbelow, the wall resonance frequencies are sharp and the apparatus may move off of the frequency band if not occasionally checked. One way to make this measurement is to sweep the frequency and observe the interferometric-like spectrum. An alternative is to transmit a fast frequency chirp, the entire frequency sweep being completed in about 100 μs (the total transit time through the liquid is approximately 55 μs for a 3 inch diameter pipe), and record the time dependence of the received signal. The detected signal appears as an amplitude-modulated signal with the signal becoming large when the frequency approaches any of the resonance frequencies. If the frequency is swept slowly, the resonances include both wall resonances and liquid resonances as fine structure superimposed on the interference spectrum. However, for a short duration chirp signal, only the first pass of the burst through the pipe diameter from source to receiver may be captured (by discarding subsequent echoes) without significant liquid involvement. That is, if the wall thickness is small the sound is reflected many times during the duration of the chirp as it propagates through the wall, and the chirp signal having these multiple reflections embedded passes through the liquid once before it is detected, thereby having information from wall resonance but not liquid resonances.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto.

Turning now to FIG. 1A, a schematic representation of a top view of dual-element piezoelectric transducer, 10, having disk piezoelectric transducer, 12, surrounded by ring piezoelectric transducer, 14, is shown, where disk transducer 12 is used as the transmitter and ring transducer 14 is used as the receiver. The outer diameter of disk transducer 12 is chosen to be less than about 1 cm since: (1) it generates a wider signal beam spread; and (2) the transducer can be easily coupled to a curved conduit surface. FIG. 1B is a schematic representation of a top view of transducer 10 mounted on the outer surface of pipe, 16. In one embodiment, disk-shaped Plexiglas or aluminum coupler, 18, having flat surface, 20, on one side, and curved surface, 22, on the other to match the curvature of conduit 16 may be used to mount the transducer. Dual-element transducer 10 may also be directly attached to the curved conduit surface without coupler 18 without any observable degradation in the quality of the measurement. Epoxy or adhesive materials can be used to attach disk 12 or ring 14 to the outer surface of conduit 16 at any location. Advantageously, the location of the attachment is away from elbows or sharp bends.

FIGS. 1C and 1D are schematic representations of a perspective view of pipe 16 and a top view thereof, respectively, having parallel, curved piezoelectric material strips, 24a-24c, attached thereto. As an example, piezoelectric material strips about 1 cm wide, by approximately 2 cm long in the curved direction may be used. Depending on the size of the conduit, other numbers and sizes of strips may be employed. The transducer elements in both FIGS. 1A and 1B and FIGS. 2A and 2B are made broadband by coating the side of the transducers away from the pipe with a layer of tungsten-loaded epoxy. Typical center frequencies used may be between about 3 and approximately 7 MHz. Lower frequencies are used for large diameter pipes, whereas higher frequencies are more effective for smaller diameter pipes because of the penetration of the signal into the fluid inside the pipe. Broader bandwidth transducers based on 1-2-3 composite materials that do not require any back loading may also be used. As an example, standard dual-element Doppler transducers used in medical imaging applications may be used for the particle detection measurements of the present invention. In the case of the curved strip transducers shown in FIG. 1C, outer elements, 24a and 24c, may be used as receivers, while center transducer 24b is used as the transmitter. A single transducer receiver may also be used. Transducer, 28, disposed opposite to transducer 24b on pipe 16 in FIG. 1D will be explained in the discussion associated with FIG. 3, hereinbelow.

The transducers are coupled with the surface of the pipe such that the beam is generally orthogonal to the flow. This differs from available commercial systems, which do not mount the transducers orthogonally, because at 90°, the Doppler signal is theoretically zero. As stated hereinabove, the transducers may be mounted flush with the surface of the pipe but, for small transducers at least in one dimension, the beam spreads sufficiently around the axis of the transducer that the sound is not transmitted solely orthogonal to the fluid flow. This is the principal reason the Doppler signal can be detected, even when the transducers are mounted flush with the surface of the pipe, and simplifies implementation of embodiments of the present invention in the field. The beam spread (−6 dB point) is given by the following expression:

$$\operatorname{Sin}\left(\frac{\theta}{2}\right) = 0.514\left(\frac{c}{f \cdot D}\right),$$

where θ is the angle of the transmitter beam, c is the sound speed in the fluid, f is the frequency applied to the transducer, and D is the diameter of the transducer. As may be seen from the equation, and from FIG. 2A, a smaller transducer diameter generates a larger beam spread, with a portion of the beam travelling in a direction parallel to the axis of the pipe. In the radial direction, the circumferential spread of the beam tends to focus because of the curvature of the pipe. The pipe wall reduces the near-field range of the beam profile significantly and so the beam that emerges appears to be in the far field.

FIG. 2A shows the spread of the ultrasound energy along the axis of the pipe for the dual-element transducer 10, whereas FIG. 2B shows the circumferential beam profile for a large curved strip transducer 24b coupled to pipe 16. The beam does not focus down to a point as shown in the figure, but narrows. If the fluid is not highly attenuating, the sound beam will be reflected from the opposite wall of the pipe and continue to spread, making the volume of interaction larger. Particle, 30, travelling through pipe 16 in FIG. 2A is shown intercepting the sound beam from transducer 12.

The Doppler signal detected from a moving particle is given by the following equation:

$$\Delta f_d = 2f \sin\alpha \cdot \frac{V_P}{V_L},$$

where $\Delta f_d$ is the Doppler shifted signal, f is the frequency the transmitter is excited, α is the total angle of the beam spread and the fluid flow, $V_P$ and $V_L$ are the velocity of the particle flowing with the liquid and the velocity of sound in the liquid, respectively. It can be seen from the equation that the higher the flow rate, the higher the Doppler shifted signal.

Figure 3:
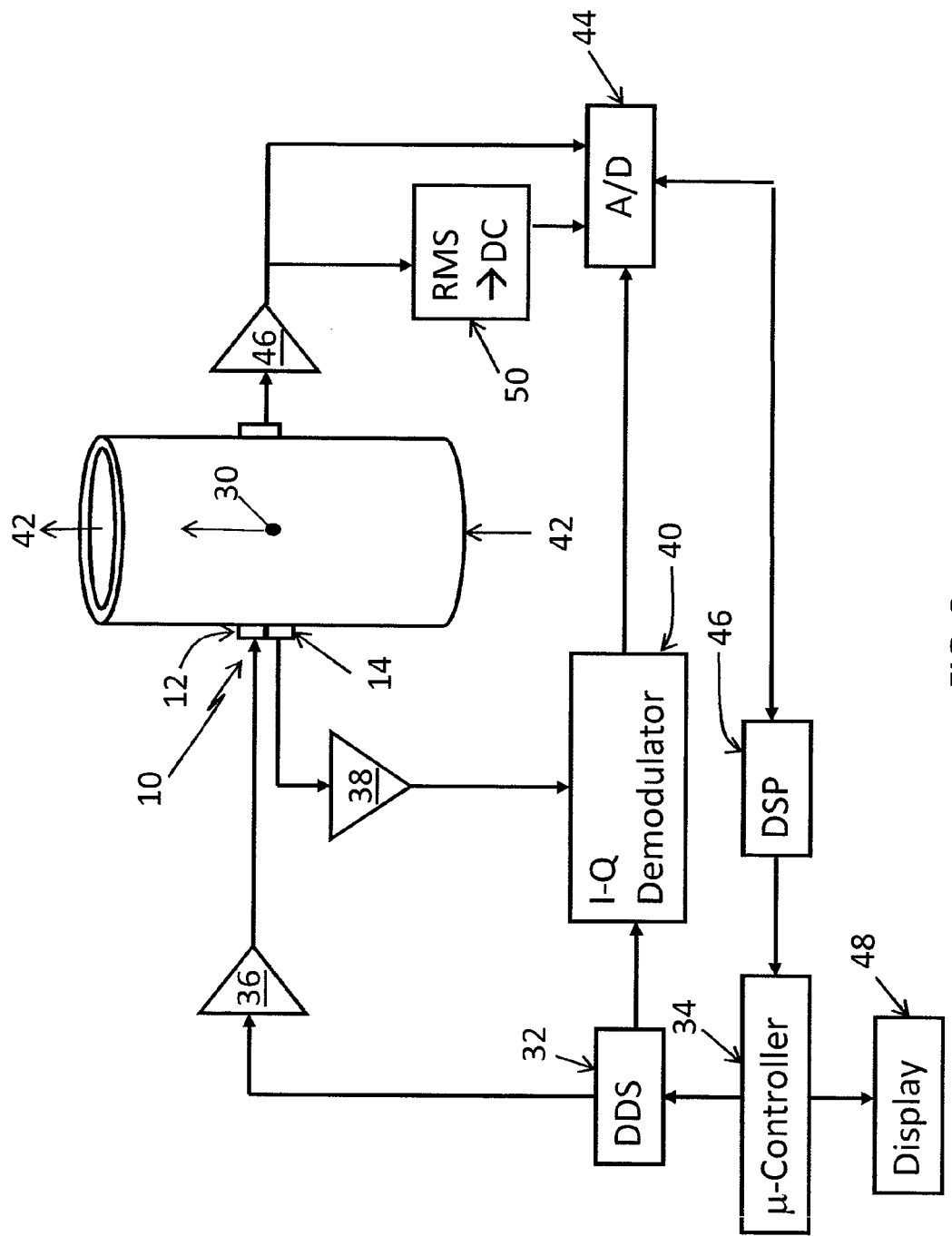
FIG. 3 is a schematic representation of an embodiment of the electronic components of the present particle detection system.

FIG. 3 is a schematic representation of one embodiment of the electronic components of the present particle detection system; it is anticipated that other configurations may be successfully implemented. Direct Digital Synthesizer (DDS), 32, controlled by microcontroller, 34, generates either a continuous-wave sine function or an intermittent-frequency chirp signal that is occasionally used. The signal is directed through buffer amplifier, 36, to transmitter transducer 12 of transducer system 10. The scattered and reflected signal detected by receiver transducer 14 (on the same side of the pipe as the transmitter transducer) is amplified by signal amplifier, 38, and directed to an in-phase and quadrature (I-Q) demodulator circuit, 40, which permits the detection of the direction of movement of solid particle, 30, or an ensemble of particles entrained in fluid flow, 42, in pipe 16. Demodulator 40 mixes the transmitted frequency in quadrature (sine and cosine output from DDS 32) with the Doppler-shifted frequency to extract the difference frequency. The demodulator includes two frequency mixers which operate at 90° from each other and output both real and imaginary parts of the Doppler signal. From this output, both the Doppler signal amplitude and phase are determined in DSP 46 following digitization by a 12 bit, 25 MHz multi-channel analog-to-digital (A/D) converter 44. The phase information provides the direction of motion information. Analog-to-digital converter 44 can be operated at a much slower rate when recording continuous measurements. The Doppler signal, which is continuously recorded in time, is converted to a joint time-frequency format so that it is possible to observe the Doppler frequency as a function of time. A spectrogram or a short-time Fourier Transform, generated from the data processed by DSP 46, and displayed by microcontroller 34 on display, 48, provides the instantaneous frequency information to obtain the Doppler frequency shift, the velocity of the particle being directly related to the Doppler shift.

Receiver transducer 28 attached to the exterior wall of pipe 16 on the opposite side of the pipe from transducer system 10, is used to determine the sound transmission characteristics of the pipe for optimizing the Doppler measurement. A frequency chirp, between about 1 MHz and approximately 10 MHz (or any smaller range) of approximately 100 μs duration, is generated by the DDS circuit and applied to the transmitter transducer. The chirp duration is not critical and other durations may also be used. The received signal on the opposite side is amplified by signal amplifier, 46, and recorded by A/D converter 44 on a different channel. A second A/D converter may be used for this measurement. The output of A/D converter 44 is directed to digital signal processor (DSP) system, 46, for processing of the chirp signal. Digital signal processor 46 also contains digital memory for data storage, and is further employed to convert the chirp signal data to the frequency domain through a Fast Fourier Transform (FFT), and also to analyze the Doppler signal data. As stated hereinabove, the frequency chirp measurement can be used for system optimization purposes to derive the wall resonance frequencies, and is used to correct for changes due to temperature or wall thinning over a long time period. During other times, the Doppler signal obtained using dual-element transducer 10 or curved transducers 24a-24c (FIG. 1C) is used in conjunction with the transmitted signal through the pipe at a fixed continuous frequency. The transmitted signal shows amplitude variation when larger numbers of particles pass through the pipe, and a combination of these two types of measurements provides robustness for the particle detection process. Additional information concerning apparatus for such analyses may be found in patent application Ser. No. 13/225,734 for "Integrated Acoustic Phase Separator And Multiphase Fluid Composition Monitoring Apparatus And Method", by Dipen N. Sinha filed on 6 Sep. 2011, the entire contents of said patent application being hereby incorporated by reference herein for all that it discloses and teaches.

As stated hereinabove, transducer 28 is used to determine the wall thickness resonances where the sound transmission is the maximum (known as transmission windows). Any of these frequencies may be used for the Doppler measurement. Higher frequencies provide higher difference frequency signals for the same particle speed, and are therefore more sensitive. However, higher frequencies also narrow the beam width of the transducer. If the pipe wall is very thick, then the resonance peaks are closely spaced and several of the individual peaks may be chosen without any noticeable difficulty. However, for thin walls, the transmission windows are far apart in frequency and the choice of frequency may be important for fine tuning the system for its most efficient operation. The present system will work reasonably well regardless of whether one chooses an appropriate transmission window. The loss in signal strength is related to the sharpness (Q, the quality factor) of the wall resonance peak, which is typically about 10 in most cases.

The output of receiver transducer 28 may also be directed to RMS→DC converter circuit, 50, that provides the root mean square (RMS) value of a continuous wave signal. This circuit makes digitization at high sample rates unnecessary when only the amplitude of the received signal is to be monitored since the RMS→DC converter provides a DC value that corresponds to the instantaneous amplitude value of the transmitted signal. When making measurements, the correct sound transmission window and the particular operating frequency within the sound transmission window are periodically determined. Once the frequency is selected, a continuous wave signal is generated and measurements are made for both Doppler and sound transmission.

Figure 4:
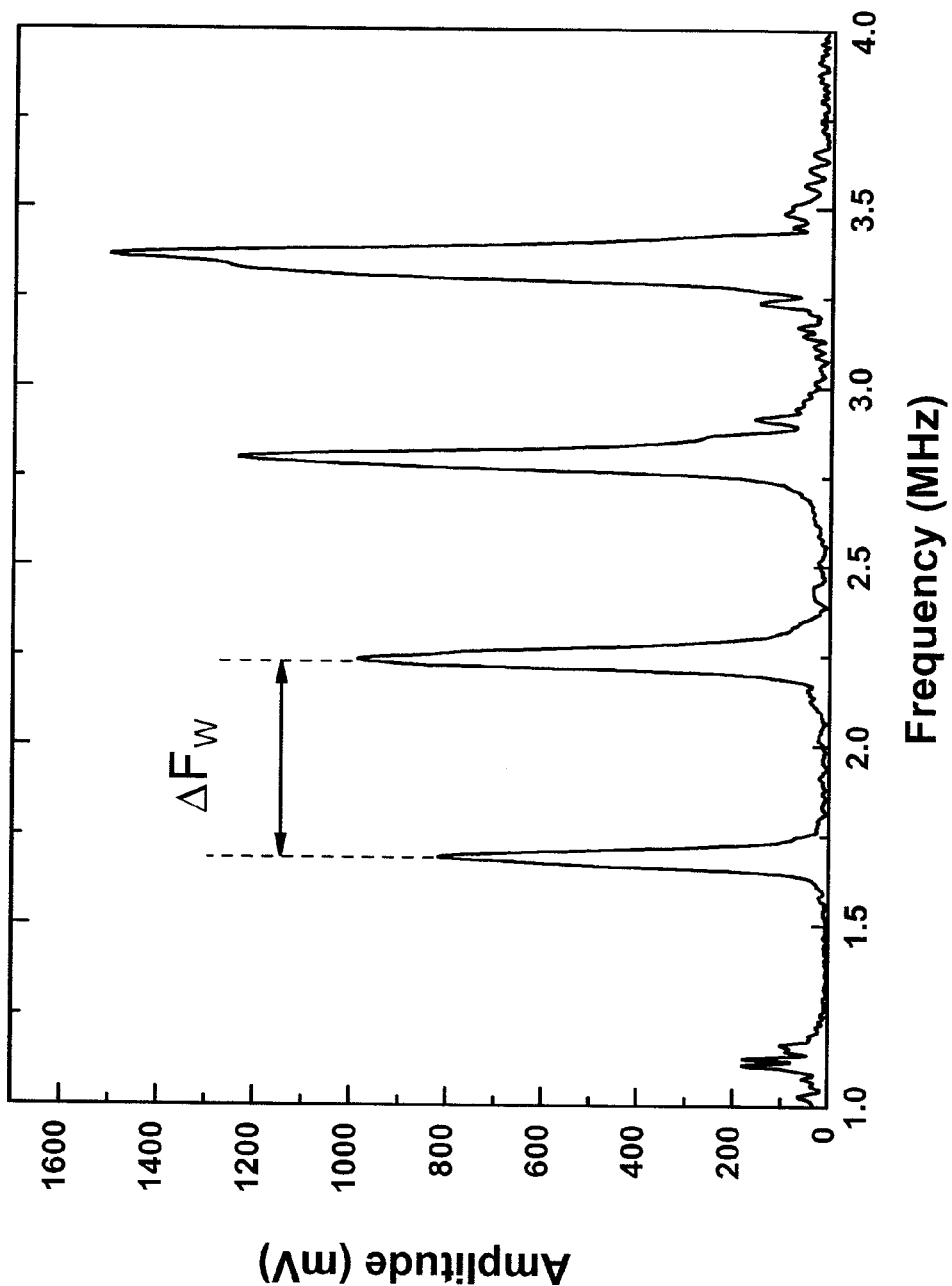
FIG. 4 is a graph of the sound transmission characteristics of a pipe wall as a function of frequency in accordance with an embodiment of the present invention.

FIG. 4 shows a graph of the Fast Fourier Transform (FFT) of a frequency chirp signal that is detected by receiver transducer 28 on the opposite side of pipe 16 from transmitting transducer 12, as a function of frequency. This graphs shows a periodic pattern of equally spaced resonance peaks in frequency, $\Delta_{FW}$, where the frequency difference is related to the thickness of the pipe wall. The data shown is for a 3-inch diameter stainless steel pipe having a wall thickness of 0.25 in. Any of the resonance peak frequencies may be used for the making the Doppler measurement, the choice depending on the particular application. The spectrum up to 4 MHz is shown but the resonance peaks continue to higher frequencies as well. Doppler measurements can be made at any frequency, but choosing higher transmission frequencies provides a stronger Doppler signal. As stated hereinabove, these so-called transmission windows also provide band-pass filtering of the data, whereby the measurements are less sensitive to external noise; that is the ambient noise is largely rejected. The DSP processed data are sent to the microcontroller for display of the results, or triggering alarms for particle detection. Additional information concerning data analysis may be found in patent application Ser. No. 13/226,444 for "Method For Noninvasive Determination Of Acoustic Properties Of Fluids Inside Pipes", by Dipen N. Sinha et al. filed on 6 Sep. 2011, the entire contents of said patent application being hereby incorporated by reference herein for all that it discloses and teaches.

If the temperature of the liquid changes significantly (for example during steam injection to loosen the oil down hole), the temperature of the pipe wall changes and the resonance frequencies shift slightly. From FIG. 4, it is observed that the resonance frequencies are sharp and a small change in wall temperature the fixed applied frequency can fall outside of the frequency window, if not occasionally checked. As stated hereinabove a fast frequency chirp is applied to the pipe—meaning the entire frequency sweep is completed in 100 µs—and the transmitted signal recorded as a function of time. The resulting signal appears as an amplitude-modulated signal with the signal becoming large each time it approaches a resonance frequency. An FFT of this time recording yields the data in FIG. 4. Another way to make this measurement would be to sweep the frequency and observe the spectrum of FIG. 4.

Having generally described embodiments of the present invention, the following EXAMPLE provides additional details.

EXAMPLE

Figure 5:
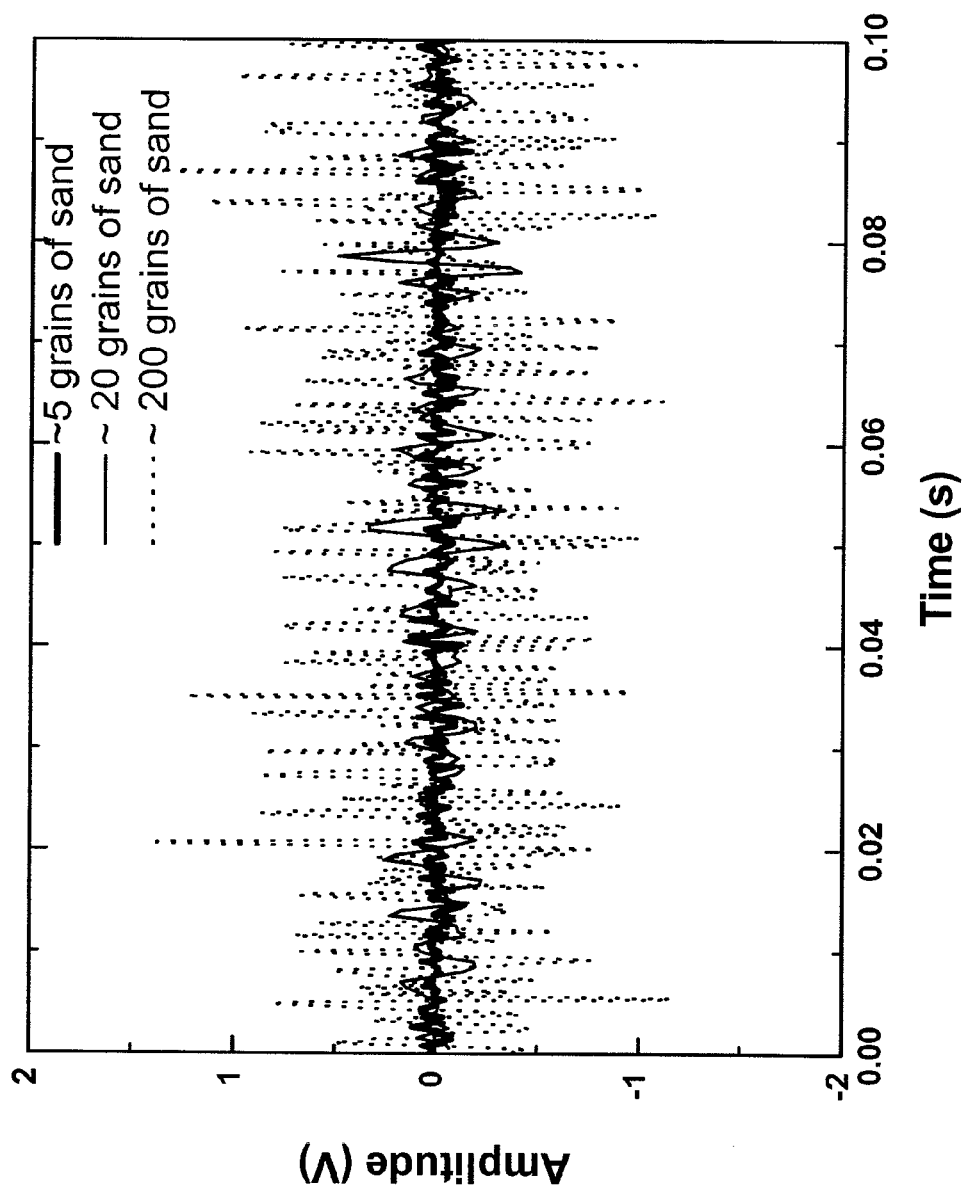
FIG. 5 is a graph of the Doppler detection of various grain amounts of 50 μm-size solid particles flowing in water, as a function of time.

FIG. 5 is a graph of the Doppler detection (where the Doppler shift frequency is converted to voltage) of various grain amounts of 50 µm-size solid particles flowing in water inside a 3 in. diameter ID pipe, as a function of time. The number of particles (5, 20, and 200) in each flow measurement is an approximate value. Clearly, a very few grains (~5 particles) of sand can be detected. The signal level increases with the number of particles such that as the number of scatterers increases, the reflected signal increases. The amplitude represents the raw signal from the instrument. The measurements are made in a 3-in. diameter ID steel pipe with a wall thickness of 0.25 in. at a frequency of 7 MHz.

Figure 6A:
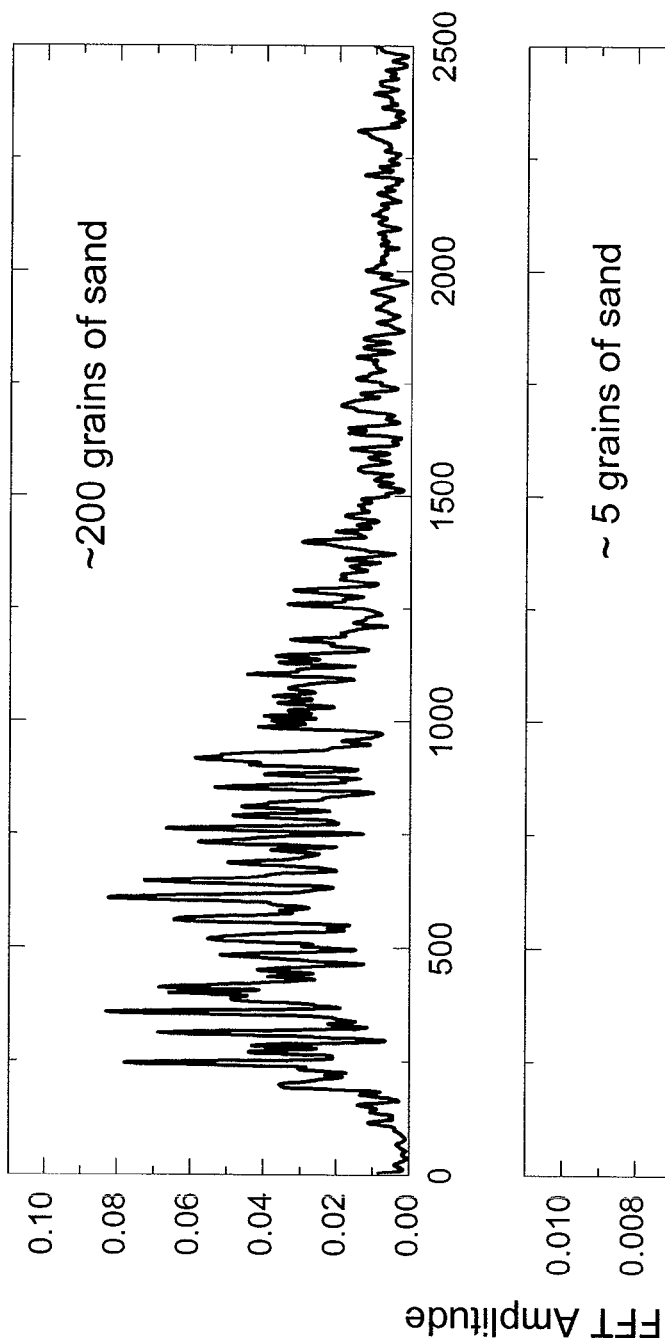
FIG. 6A is a graph of the FFT of the data shown in FIG. 5 hereof for approximately 200 grains of sand, and FIG. 6B for 5 grains of sand.
Figure 6B:
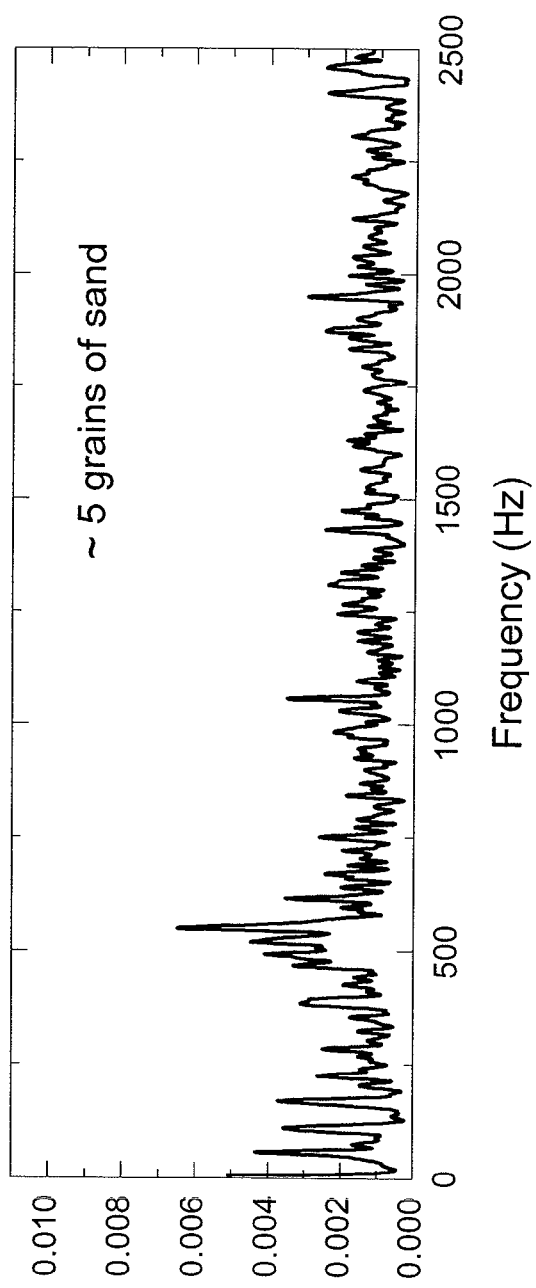

FIG. 6A is a graph of the FFT of the data shown in FIG. 5 hereof for approximately 200 grains of sand, and FIG. 6B for 5 grains of sand. The y-axis is the FFT amplitude of the signal, and is related to velocity of the particles. A few grains of sand pass through the detection region quickly, whereas a larger number of particles traverse the sound beam more slowly as the particles are spread over a slightly wider spatial region. FIGS. 6A and 6B demonstrate that the very early stage of sand production can be detected using the present method. The integrated area under the curve provides a measure of the number of particles present. The detection limit for the apparatus employed is about 20 particles per milliliter, and measureable particle sizes can be as small as approximately 1 µm. To obtain the data shown in FIGS. 6A and 6B, an operating frequency of 9.4 MHz was used.

Figure 7B:
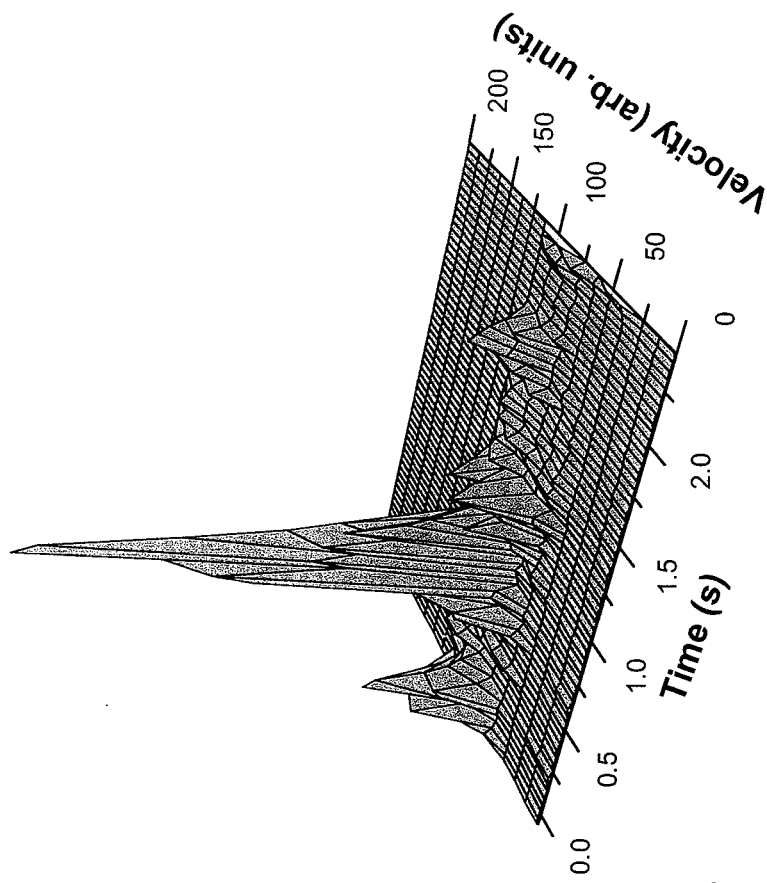
FIG. 7B is a joint time-frequency contour plot that shows the velocity of the particles as a function of time.
Figure 7A:
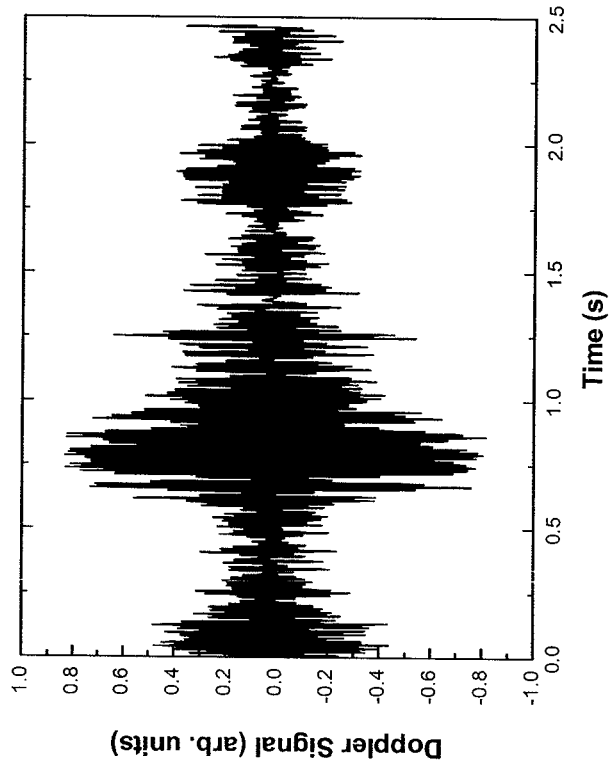
FIG. 7A shows the actual raw Doppler data from the measurement system for 25 micron size particles passing through the system of FIG. 3.

A suspension of 0.15 g of 25 µm (800 grit) particles was made in 30 mL of water and was slowly injected into a 2-inch diameter stainless steel pipe with the water flowing at a rate of about 0.15 gallon per min. The unprocessed raw Doppler signal is shown in FIG. 7A. Since the injection process for the suspension was not uniform, bursts appear in the measured data. FIG. 7B shows a joint time and frequency plot derived from the data in FIG. 7A, where the particle velocity signal is presented as a function of time. Although the particle velocity remains approximately the same, the particle flow comes in bursts because of the injection process. This flow rate is quite slow and the Doppler signal is expected to be much greater when higher flow rate is used.

Figure 8B:
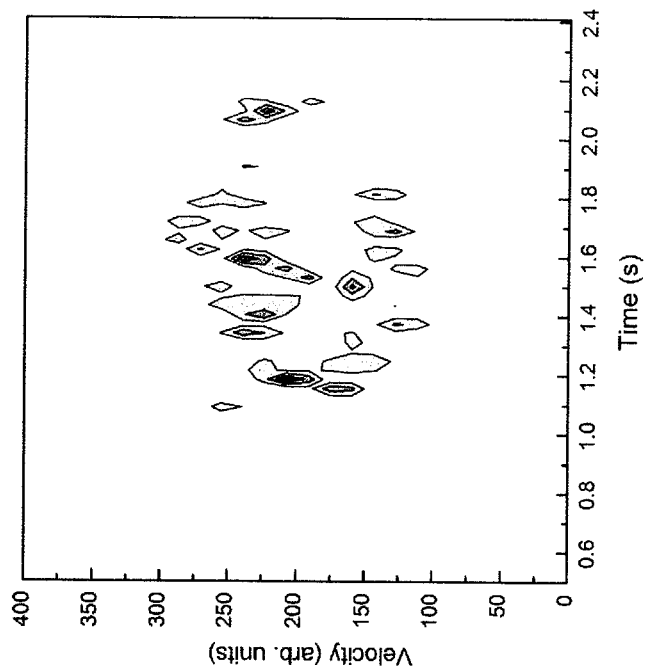
FIG. 8B is a graph of the velocity as a function of time.
Figure 8A:
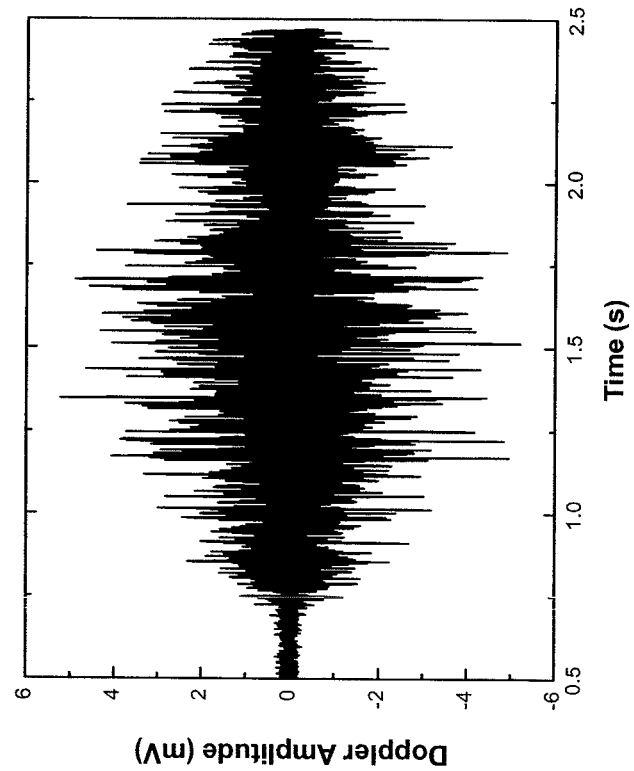
FIG. 8A shows the actual raw Doppler data from the measurement system of FIG. 3 for particle sizes of 45 μm.

A suspension of 0.03 g of 45 µm (320 grit) particles in 30 mL of water was injected into a 2 in. diameter stainless steel pipe with the water flowing at a rate of about 0.15 gallon per min., and the raw Doppler signal is shown in FIG. 8A. The velocity-time plot of the same data is shown as a contour plot in FIG. 8B, which shows a spread of the velocity likely due to particles clumping together during the injection process.

FIGS. 9A-9C are graphs of measurements where oil/water foam was introduced in to the system. FIG. 9A shows that when only water is present without particles, there is no Doppler signal. When 3.28 µm latex particles were introduced into the flowing water, a Doppler signal is readily detected as is observed in FIG. 9B. The foam produced a different and unique Doppler signal, as may be observed in FIG. 9C. Thus, an FFT of the raw Doppler signal carries information concerning the particle size and type.

The observation of simultaneous Doppler and sound transmission measurements is not shown in the drawings, but is an additional aspect of the present invention. The transmitted signal is sensitive to the presence of particles in the volume of liquid between two opposing transducers. However, small quantities (for example, <5 grains) of small particles (for example, <1 µm) are not reliably detected by this approach. When a burst of particles (either particles having larger size or a larger number of smaller particles) passes through the measurement region, the transmitted signal amplitude decrease corresponding to the presence of the particles, thereby providing an additional corroboration of particle or sand presence, and can be used as an alarm trigger when large numbers of particles suddenly pass through the pipe.

Although the measurements presented are for water, the same measurements were repeated in mineral oil with similar results. In mineral oil as well as water, even a small number of particles flowing in pipe could be detected in a noninvasive manner at excitation frequencies as low as 1 MHz. However, higher frequencies typically provide better signals. Higher flow rates also generate larger Doppler shifts.

As stated hereinabove, the Doppler spectrum determines particle size and distribution. In fluid-particle flows the Stokes number is the ratio of the response time of a particle, the time that a particle takes to respond to a change in carrier flow velocity, to a time characteristic of a flow system. If the Stokes number is less than 0.1, the particles have sufficient time to respond to the change in fluid velocity, and the particle velocity approaches the fluid velocity. By contrast, if the Stokes number is greater than 10, the particles have little time to respond to the varying fluid velocity and the particle velocity shows little corresponding change. The relative concentration of the particles in the fluid is referred to as loading, which may be defined as the ratio of particle mass flow to fluid mass flow. If the particle loading is small, the fluid will affect the particle properties (velocity, temperature, and so forth), but the particles will not influence the fluid properties, and is referred to as one-way coupling. If the conditions are such that there is a mutual interaction between the particles and fluid, the flow is two-way-coupled.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for noninvasively measuring the velocity and direction of travel of at least one particle suspended in a fluid flowing in a pipe having an axis and a wall, comprising:
    a first transducer flush with and in vibrational communication with an outside surface of said pipe at a chosen position along the axis thereof;
    a signal generator for providing a chosen signal having at least one selected frequency to said first ultrasonic transducer, wherein vibrations are generated in said fluid at least a portion of which vibrations are in the direction of flow of said fluid, and an equal portion thereof are opposite the direction of flow of said fluid;

a second transducer flush with and in vibrational communication with an outside surface of said pipe disposed alongside said first transducer at the chosen position along the axis for detecting a scattered vibration signal from said at least one particle;

an in-phase and quadrature demodulator for processing the detected scattered signal from said at least one particle;

a multichannel analog-to-digital converter a microcontroller; and a digital signal processor controlled by said microcontroller for performing a joint time and frequency analysis of the detected scattered signal from said at least one particle from which a signal amplitude for said at least one particle, and a Doppler frequency shift and a phase shift between the detected scattered signal from said at least one particle and the chosen vibration signal generated by said first transducer, are obtained as a function of time;

whereby velocity and direction of travel of said at least one particle are measured.

2. The apparatus of claim 1, further comprising:

a third transducer in vibrational communication with an outside surface of said pipe and diametrically opposed to said first transducer for detecting vibrations directed into said liquid from said first transducer;

a signal generator for providing a frequency chirp signal to said first transducer having a duration less than the time for a vibration generated in said liquid to reach said third transducer from said first transducer; and a signal processor for receiving the chirp signal;

whereby resonant vibrations in the wall of said pipe are detected.

3. The apparatus of claim 2, wherein said signal processor fast Fourier transform the received chirp signal.

4. The apparatus of claim 2, wherein the at least one selected frequency corresponds to a resonant vibration in the wall of said pipe.

5. The apparatus of claim 1, wherein the generated vibrations have a frequency of >1 MHz.

6. The apparatus of claim 2, wherein said first transducer, said second transducer, and said third transducer comprise piezoelectric transducers.

7. The apparatus of claim 1, wherein said in-phase and quadrature demodulator further determines the amplitude of the scattered signal from which the number of particles is determined.

8. A method for noninvasively measuring the velocity and direction of travel of at least one particle in a fluid flowing in a pipe having an axis and a wall, comprising:

generating vibrations having at least one chosen frequency in said fluid in the direction of fluid flow, using a first transducer flush with and in vibrational communication with an outside surface of said pipe and a chosen position along the axis thereof, driven at the at least one chosen frequency, wherein vibrations are generated in said fluid at least a portion of which vibrations are in the direction of flow of said fluid, and an equal portion thereof are opposite the direction of flow of said fluid;

detecting a scattered vibration signal from said at least one particle, using a second transducer flush with and in vibrational communication with an outside surface of said pipe disposed alongside said first transducer at the chosen position along the axis;

processing the detected scattered signal from said at least one particle using an in-phase and quadrature demodulator;

performing a joint time and frequency analysis to obtain an amplitude and a Doppler frequency shift and phase shift between the scattered signal from said at least one particle and the at least one chosen frequency of the first transducer for said at least one particle as a function of time; and monitoring the Doppler frequency shift between the scattered vibration signal from said at least one particle and the chosen frequency of the generated vibrations;

whereby velocity and direction of travel of said at least one particle are measured.

9. The method of claim 8, wherein the number of particles is determined from the amplitude of the detected scattered signal.

10. The method of claim 8, further comprising the step of selecting the at least one chosen frequency to be the frequency of a resonant wall vibration.

11. The method of claim 10, wherein said step of selecting the at least one chosen frequency is performed using a third transducer in vibrational communication with an outside surface of said pipe and diametrically opposed to the first transducer for detecting vibrations directed into said liquid from the first transducer, and driven by a signal generator for providing a frequency chirp signal to the first transducer having a duration less than the time for a vibration generated in said liquid to reach the third transducer from the first transducer; and a signal processor for receiving the chirp signal from the third transducer, whereby resonant wall vibrations are detected.

12. The method of claim 11, further comprising the step of fast Fourier transforming the received chirp signal.

13. The method of claim 12, wherein said step of fast Fourier transforming the received chirp signal is performed using a signal processor receiving the chirp signal from the third transducer.

14. The method of claim 8, wherein the at least one chosen frequency is >1 MHz.

15. The method of claim 11, wherein said first transducer, said second transducer, and said third transducer comprise piezoelectric transducers.

* * * * *